United States Patent [19]

Kempen

[11] Patent Number: 4,751,219

[45] Date of Patent: Jun. 14, 1988

[54] SYNTHETIC GLYCOLIPIDES, A PROCESS FOR THE PREPARATION THEREOF AND SEVERAL USES FOR THESE SYNTHETIC GLYCOLIPIDES

[75] Inventor: Hermanus J. M. Kempen, Leiden, Netherlands

[73] Assignee: Nederlandse Centrale Organisatie Voor Toegepast-Natuur-Wetenschappelijk Onderzoek, The Hague, Netherlands

[21] Appl. No.: 698,325

[22] Filed: Feb. 5, 1985

[51] Int. Cl.⁴ ............... A61K 9/08; A61K 31/66; A61K 31/70

[52] U.S. Cl. .................................. 514/26; 536/5; 424/450; 424/461

[58] Field of Search ............... 514/26; 536/5; 424/450, 424/461

Primary Examiner—Ronald W. Griffin
Attorney, Agent, or Firm—Rosen, Dainow & Jacobs

[57] ABSTRACT

Synthetic glycolipides having the general formula lipidyl-O-R wherein the lipidyl moiety is selected from the group consisting of 5-cholestene-3β-yl, ceramidyl, phosphatidylethanolamine and diacylglycerol and R represents a group having the formula

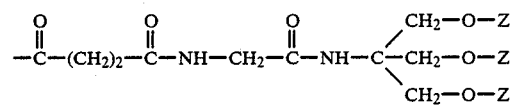

in which two symbols Z represent a glycopyranosyl rest and the other symbol Z a hydrogen atom or all three symbols Z represent a glycopyranosyl rest. These new glycolipides can be used for the solubilization of cholesterol in water or aqueous media, for the manufacture of lipide-vesicles or lipoproteins in which such a glycolipide is encapsulated as well as for the reduction of the cholesterol level in the blood plasma of mammals. Preferably the compound N-tris(β-D-galactopyranosyloxymethyl)methyl-Nα-(4-(5 cholesten-3β-yloxy)succinyl)glycinamide is used.

11 Claims, 6 Drawing Sheets

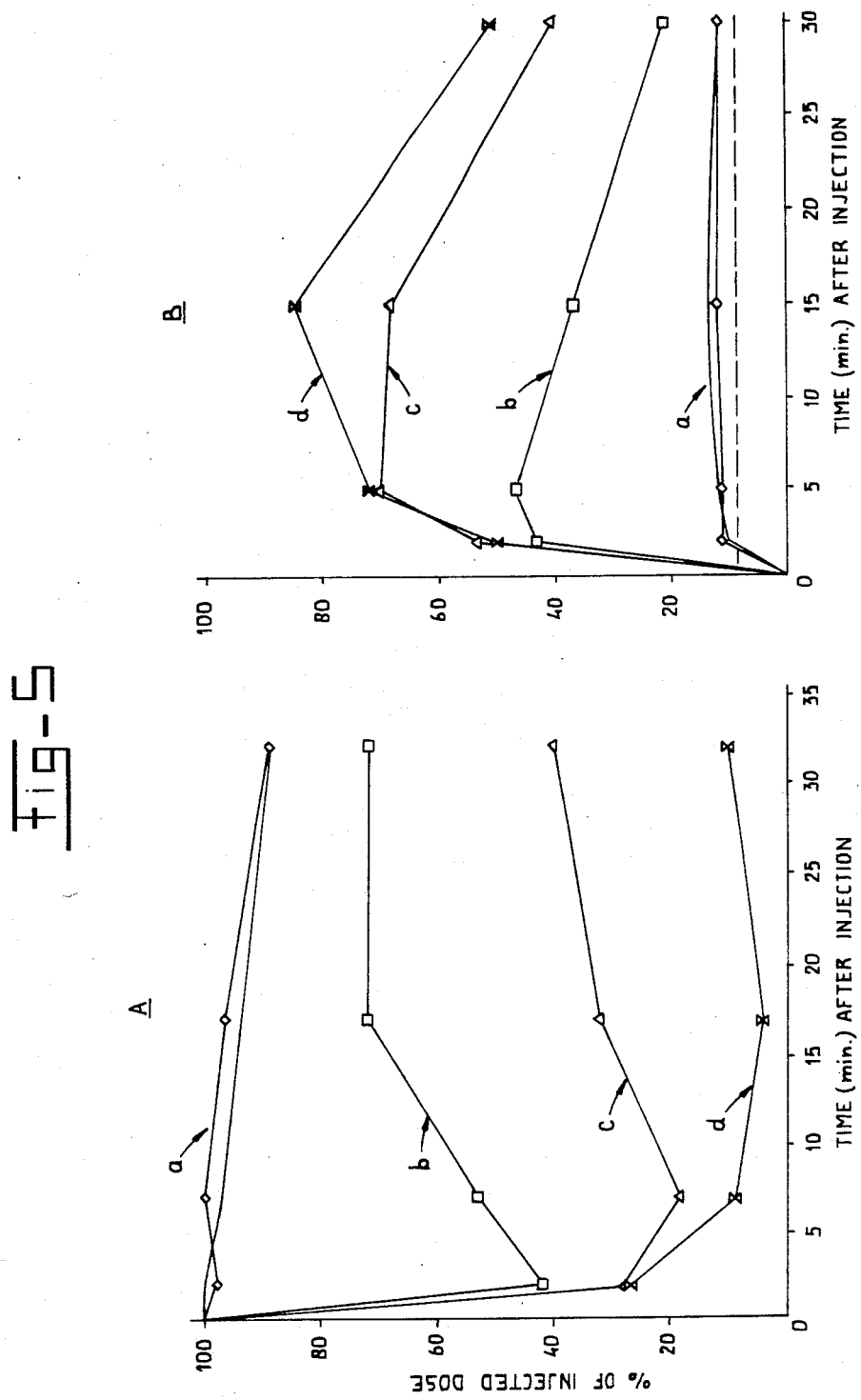

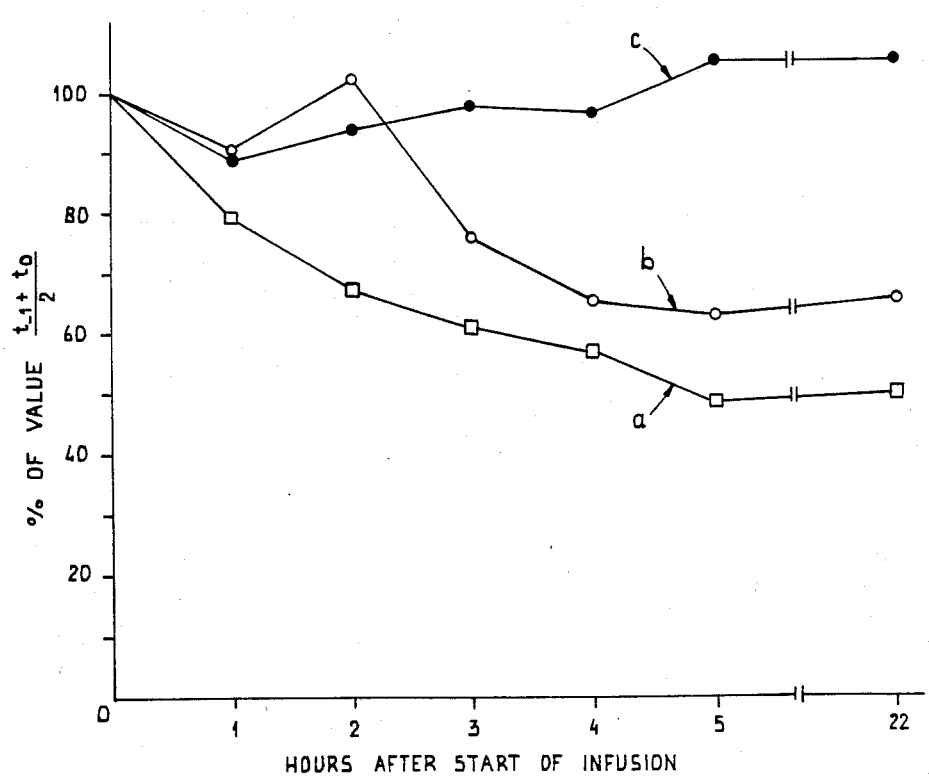

SYNTHETIC GLYCOLIPIDES, A PROCESS FOR THE PREPARATION THEREOF AND SEVERAL USES FOR THESE SYNTHETIC GLYCOLIPIDES

The invention relates to synthetic glycolipides which may be used for increasing the uptake of lipide-vesicles or lipoproteins by organs in living organisms.

Such glycolipides which increase the uptake by organs are known. Examples thereof are cholesterylglycosides (Chabala and Shen, Carbohydr. Res. 67: 55-63, 1978; Ponpipom et al., Can. J. Chem. 58: 214-220, 1979; Slama and Rando, Carbohydr. Res. 88: 213-221, 1981; European Pat. No. 0029917 A2), lactosylcerebrosides or gangliosides (Bussian and Wriston, Biochim. Biophys. Acta 471: 336-340, 1977; Jonah et al., Biochim. Biophys. Acta 541: 321-333, 1978; Surolia and Bacchawat, Biochim. Biophys. Acta 497: 760-765, 1977; Hoekstra et al., Biochim. Biophys. Acta 603. 336-346, 1980; Spanjer and Scherphof, Biochim. Biophys. Acta 734: 40-47, 1983) and chemically modified phosphatidylethanolamine (Gosh and Bacchawat, Biochim. Biophys. Acta 632: 562-572, 1980; Gosh et al., Arch. Biochem. Biophys. 206: 454-457, 1981).

These known glycolipides have the disadvantage that they are not water-soluble. For encapsulating them in lipide-vesicles together with other lipides (for instance phosphatidylcholine or sphingomyeline and cholesterol) these compounds should be dried as a film from an organic solvent and then dispersed in an aqueous medium by mechanical agitation and ultrasonic radiation. For encapsulating in lipoproteins these glycolipides should first be fixed on glass grains from an organic solvent (Loeb and Dawson, J. Biol. Chem. 257: 11982-11987, 1982).

Surprisingly applicant found new glycolipides which have the advantage that they are water-soluble and therefore can be encapsulated in lipide-vesicles or lipoproteins in a simple way. For instance these new glycolipides according to the invention can be used for
(1) solubilisation of cholesterol in aqueous media and
(2) reduction of the plasma cholesterol level in mammals. Apparently the compounds according to the invention are encapsulated in the outer layer of liposomes or lipoproteins with the effect that the clearence of these particles from the blood is enhanced.

The synthetic glycolipides according to the invention are characterized by the general formula lipidyl-O-R in which the lipidyl-moiety is selected from the group consisting of 5-cholesten-3β-yl, ceramidyl, phosphatidylethanolamine and diacylglyceryl and R represents the group having the formula:

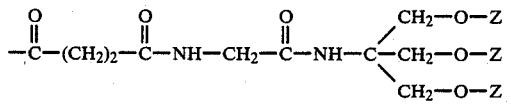

wherein two symbols Z represent a glycopyranosyl group and the other symbol Z a hydrogen atom or al three symbols Z represent a glycopyranosyl group.

More in particular the glycolipides according to the invention are characterized by the features that the lipidyl moiety is bound (via an ester linkage) with a group R which is composed of the moieties succinic acid (a), glycine (b), tris(hydroxymethyl)aminomethane (c) and two or three glycopyranosyl groups (d).

As indicated in the above the lipidyl moiety can be derived from cholesterol, ceramide, phosphatidylethanolamine or diacylglycerol. As glycopyranosyl groups the hexoses known from the literature like glucose, mannose, galactose etc. can be chosen.

With respect to the names "phosphatidylethanolamine" and "ceramide" it is referred to Harper's Review of Biochemistry, 18th Edition, respectively pages 190 and 191; the fatty acids present in these types of compounds may, independently from each other, be saturated or unsaturated and contain preferably 10-22 carbon atoms.

The acyl groups in the diacylglyceryl group used as lipidyl moiety may be different from each other and may be saturated or unsaturated. Preferably these acyl groups contain 10-22 carbon atoms. Particularly 1.2-diacylglyceryl groups are used according to the invention.

In the case that the glycolipide according to the invention is used for enhancing the uptake of lipide-vesicles or lipoproteins from the blood by the liver the monohexose is preferably galactose or derivatives thereof like 2-acetamido-2-deoxygalactose.

The encapsulating of the glycolipides according to the invention in lipide-vesicles or lipoproteins can be carried out in a simple way. For that purpose the compound according to the invention is dissolved in water or an aqueous salt solution and this solution is mixed with a suspension of lipide-vesicles or lipoproteins in water or an aqueous salt solution.

When a glycolipide according to the invention is used for the solubilisation of cholesterol in water or aqueous media the compound may contain three optional glycopyranosyl-moieties.

The invention also relates to a process for the preparation of the instant glycolipides. This process is characterized by the following stages:

(a) N(2-hydroxy-(1,1-dihydroxymethyl)-ethyl)-Nα-benzyloxycarbonylglycinamide is prepared in a way known per se by reacting 2-amino-2-hydroxymethyl-1,3-propanediol with benzyloxycarbonylglycine in the presence of N-ethoxycarbonyl-2-ethoxy-1,2-dihydroquinoline;

(b) Per-O-acetyl-D-glycopyranosylbromide is prepared in a way known per se by reacting per-O-acetyl-D-glycopyranose with PB$_3$ in acetic anhydride;

(c) N-(tris(per-O-acetyl-D-glycopyranosyloxymethyl)-methyl-Nα-benzyloxy-carbonylglycinamide is prepared in a way known per se by reacting N(2-hydroxy-(1,1-dihydroxymethyl)-ethyl)-Nα-benzyloxycarbonyl-glycinamide as suspension in CH$_3$CN, together with Hg(CN)$_2$ and HgBr$_2$, with per-O-acetyl-D-glycopyranosylbromide dissolved in CH$_3$CN and purifying the product from a number of by-products by means of column chromatografy;

(d) N-(tris(per-O-acetyl-D-glycopyranosyloxymethyl)-methyl-Nα-benzyloxycarbonylglycinamide is converted in a way known per se into N-(tris(-glycopyranosyloxymethyl)methyl)glycine. HCl-salt by treating it subsequently with triethanolamine, acetic acid, hydrogen with palladium/carbon and HCl after which the product is purified by gelfiltration;

(e) One of the lipids selected from the group consisting of cholesterol, phosphatidylethanolamine, ceramide or diacylglycerol is reacted with succinic acid in pyridine in a way known per se into the corresponding hemisuccinylester whereafter this ester is subsequently converted into the N-hydroxy-succinimidyl- 4-(lipidyl)succinate by reacting said ester with N-hydroxysuccinimide in tetrahydrofuran in the presence of dicyclohexylcarbodiimide in a way known per se;

(f) N-(tris(glycopyranosyloxymethyl)methyl)-$N^\alpha$-(4-lipidyl)succinylglycinamide is obtained by reacting N-(tris(glycopyranosyloxymethyl)methyl)-glycine.HCl-salt, dissolved with N-ethylmorpholine in dimethylformamide with N-hydroxy-succinimidyl-4-(lipidyl)succinate dissolved in dimethylacetamide; the N-(tris(glycopyranosyloxymethyl)methyl)-$N^\alpha$-(4-lipidyl)succinyl-glycinamide according to the invention as well as the corresponding bis(-glycopyranosyloxymethyl)-derivatives are purified by column chromatography.

The invention will be elucidated by means of several examples. The compounds according to the invention are illustrated in example 1.

BRIEF DESCRIPTION OF THE DRAWINGS

FIGS. 1–6 illustrated results concerning several uses. It is emphasized that the invention may not be restricted to the contents of the following examples.

EXAMPLE 1

Figure 1:
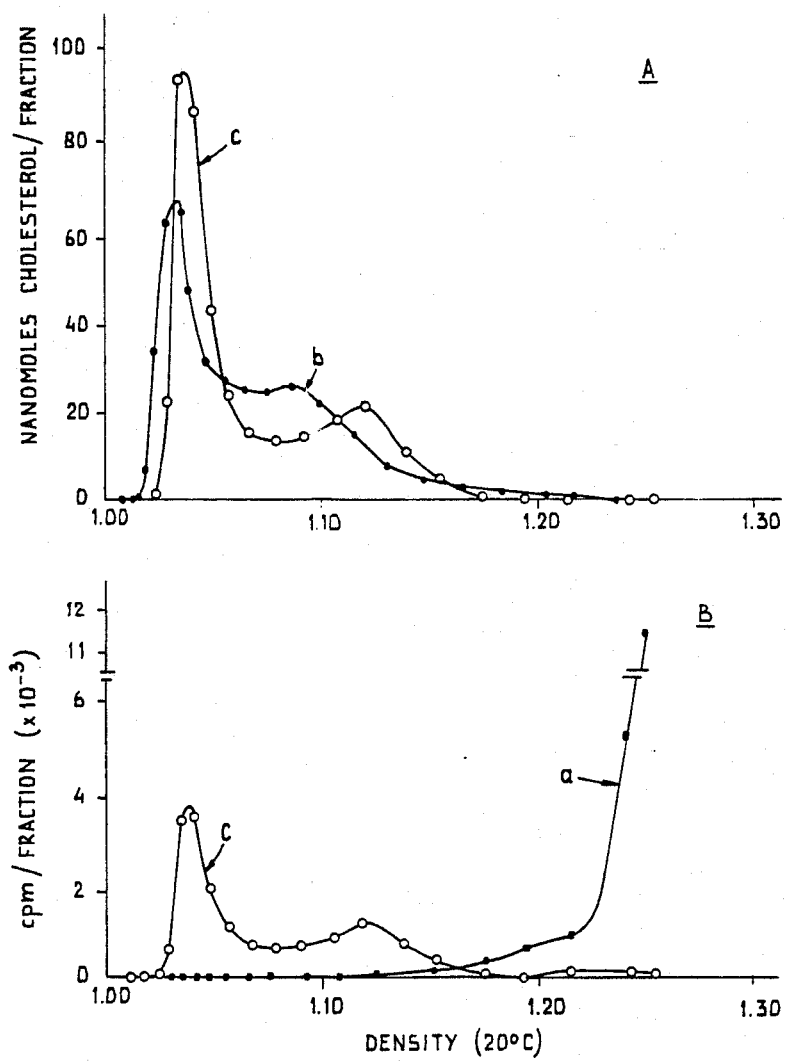

The compound N-(tris($\beta$-D-galactopyranosyloxymethyl)methyl-$N^\alpha$-(4-(5-cholesten-3$\beta$-yloxy)succinyl-glycinamide is prepared via the following stages: (the mentioned starting compounds are trade compounds, p.a.-quality).

(a) To a stirred and cooled (ice-water bath) solution of 25 g (64 mmol) of penta-O-acetyl-D-galactopyranose and 38.4 ml PBr, in 128 ml acetic anhydride was added dropwise 54 ml of water during a period of 90 minutes. The compound 2.3.4.6-tetra-O-acetyl-$\beta$-D-galactopyranosylbromide having formula 1

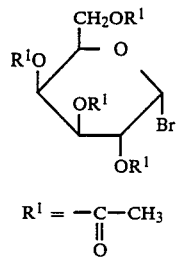

was obtained from this mixture by the addition of 450 ml of chloroform, extraction with 4×500 ml of cooled water, 2×500 ml of cooled 7% NaHCO$_3$-solution and 2×500 ml of water, separation of the chloroform layer, drying of the chloroform layer with MgSO$_4$ and evaporation of the chloroform. The residue was crystallised once in diisopropylether/hexane. Yield: 17.9 g (43.5 mmol; 68%).

(b) The compound having formula 2

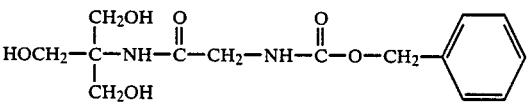

was prepared by refluxing a solution of 6.1 g (50 mmol) of 2-amino-2-hydroxymethyl-1.3-propanediol, 11.5 g (55 mmol) benzyloxycarbonylglycine and 14.8 g (60 mmol) of N-ethoxycarbonyl-2-ethoxy-1.2-dihydroquinoline in 500 ml of absolute ethanol for 6 hours. The mixture was cooled and the ethanol was removed by destillation under reduced pressure. To the obtained syrup 250 ml of diethylether was added under good stirring. The precipitate was collected by filtration, washed with diethylether, dried and dissolved in 100 ml of methanol. Dowex grains 50×4 (H-form) were added until the pH was neutral. The grains were removed and the solution was evaporated until an almost dry product. The compound having formula 2 was crystallised by the addition of diethylether. Yield: 7.5 g (24 mmol; 48%).

(c) A mixture of 3.1 g (10 mmol) of compound having formula 2, 3.8 g (15 mmol) Hg(CN)$_2$ and 5.4 g (15 mmol) of HgBr$_2$ in 100 ml CH$_3$CN was stirred at room temperature. To this suspension a solution of 12.3 g (30 mmol) of compound having formula 1 in 100 ml of CH$_3$CN was added dropwise during 30 minutes. Hereafter the reaction mixture was stirred another 60 minutes whereby the reaction mixture gradually cleared. Then additional portions of 4.1 g (10 mmol) of the compound having formula 1, 1.3 g of Hg(CH)$_2$ and 1.8 g of HgBr$_2$ were added. The mixture was stored overnight at room temperature and then evaporated to dryness. The residue was suspended in 350 ml of CHCl$_3$, the suspension was washed with 5×125 ml of 1M KBr and 5×120 ml of water. The CHCl$_3$-extract was dried by using MgSO$_4$ and evaporated to dryness. The obtained residue appeared to contain besides the compound having formula 3

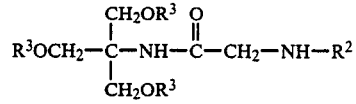

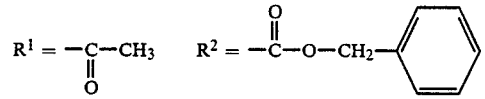

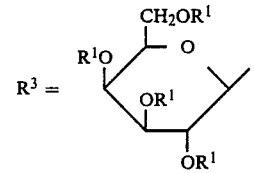

a number of by-products. The compound having formula 3 was purified by column chromatography on silica with CHCl$_3$/acetone (8/2) as eluant. The fraction containing the compound having formula 3 were combined and evaporated to dryness. This purification was repeated with CHCl$_3$/acetone(82/18) as eluant. The fractions containing only the compound having formula 3 were combined and evaporated to dryness. Yield: 3.1 g (2.37 mmol); 32%).

(d) To a solution of 2.68 g (2.05 mmol) of the compound having formula 3 in 25 ml of methanol were added 25 ml of water and 3.43 ml (25 mmol) of triethanolamine. The solution was stirred for 120 minutes at room temperature and acidified with 1.4 ml (25 mmol) of acetic acid. The mixture (deacylated compound 3) was evaporated by distillation under reduced pressure and then lyophilized. The dry material (2.95 mmol) was dissolved in 100 ml of acetic acid/water (6/4) and flushed with nitrogen gas. After addition of 0.9 g of 10% Pd/carbon hydrogen was led through the solution at atmospheric pressure. The catalyst was removed by filtration and the filtrate lyophilized. In order to separate the compound having formula 4

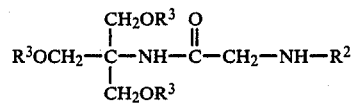

4.

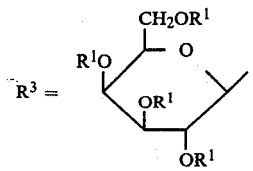

from the triethanolamine-acetate (obtained during the de-acylating) the residue was eluated on a Sephadex G-10 column with 0.1M acetic acid as eluant. The fractions with the compound having formula 4 devoid of triethanolamine were combined and lyophilized. The compound was converted into the chloride by dissolving the residue in 0.01M HCl (excess) and lyophilized again. Yield: 1.03 g (1.47 mmol; 72% based on the compound having formula 3).

(e) 2.4 of (11 mmol) Dicyclohexylcarbodiimide was added to a solution of 5 g (10.2 mmol) cholesteryl hydrogen succinate and 1.23 g (10.7 mmol) N-hydroxysuccinimide in tetrahydrofuran. The mixture was stirred for 60 minutes at −10° C. and for another 180 minutes at room temperature and then stored for 12 hours at 4° C. The precipitate was removed by filtration. The filtrate was evaporated to dryness and the obtained product having formula 5

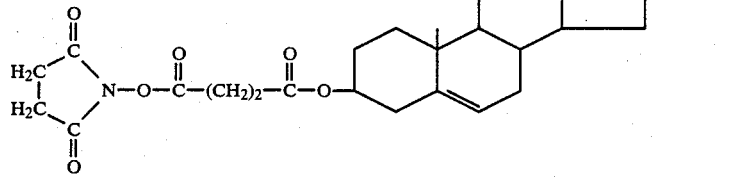

was crystallized from tetrahydrofuran/2-propanol. Yield: 5.3 g (9.1 mmol; 89%).

(f) 430 mg (0.614 mmol) of the compound having formula 4 was dissolved in 15 ml of dimethylformamide. To said solution 163 μl (1.30 mmol) of N-ethylmorpholine was added. Subsequently a solution of 553 mg (0.95 mmol) of the compound having formula 5 in 19 ml of dimethylacetamide was added. This mixture was stirred for 210 minutes at room temperature after which the mixture was acidified with 77 μl (1.34 mmol) of acetic acid and evaporated to practically complete dryness. Then 50 ml of tetrahydrofuran was added and the resulting precipitate was collected by filtration, washed with 40 ml of tetrahydrofuran and 40 ml of diethylether and dried above solid KOH in vacuo. A solution of the material in water was lyophilized. Yield: 603 mg of crude product in which besides the compound having formula 6 (main component)

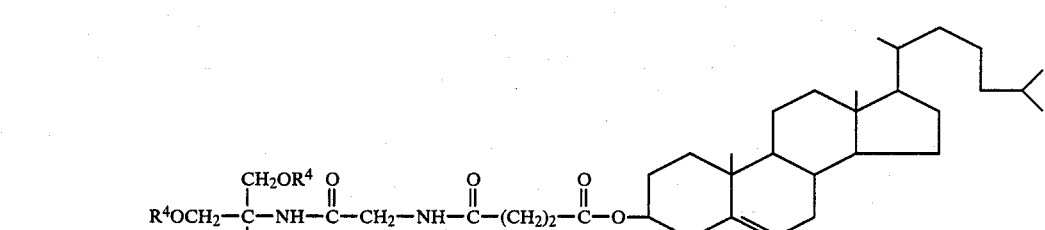

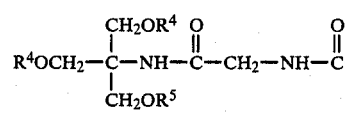

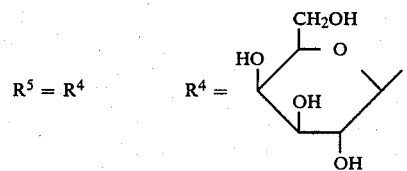

the corresponding bis(galactosyloxymethyl) derivative having formula 7 (by-component)

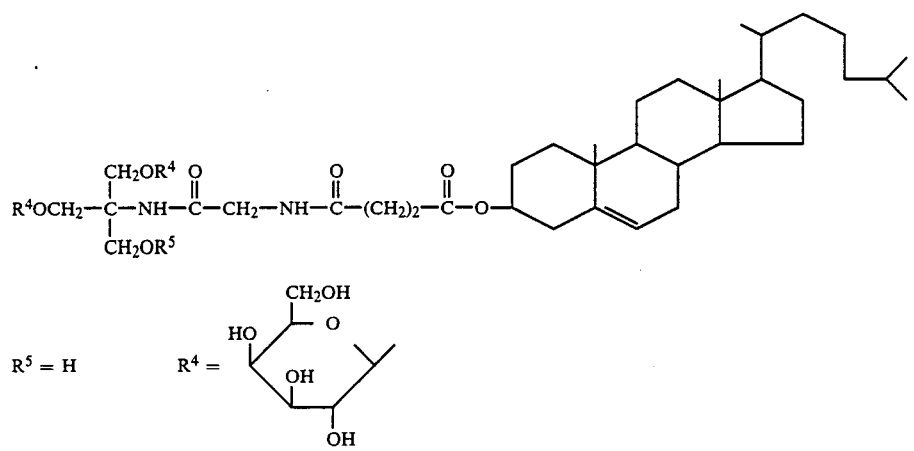

was identified.

(g) Separation of the compounds having formulas 6 and 7 was achieved by chromatography on a column of silica with CHCl$_3$/CH$_3$OH/water (54/40/6) as eluant. Fractions containing either one of the compounds having formulae 6 or 7 were combined and evaporated to dryness. The residues were dissolved in water, filtered through Whatman GF/A paper and twice lyophilized. Yield of the compound having formula 6: 534 mg (0.471 mmol; 50% based on the compound having formula 4); yield of the compound having formula 7: 94 mg (10% based on the compound having formula 4).

EXAMPLE 2

The so prepared compound having formula 6 can be dissolved up to a concentration of 10 mM in water. After mixing of one volume part of a solution of cholesterol in ethanol with 9 volume parts of solution of 1 mM of the compound having formula 6 in water no precipitation of cholesterol occurs. The cholesterol does not even precipitate after dialysis but remains in solution within the dialysis tube. However, such a precipitation occurs to a mixture of cholesterol dissolved in ethanol with water. This example illustrates that the compound having formula 6 is able to solubilize cholesterol in water or aqueous media.

EXAMPLE 3

Figure 2:
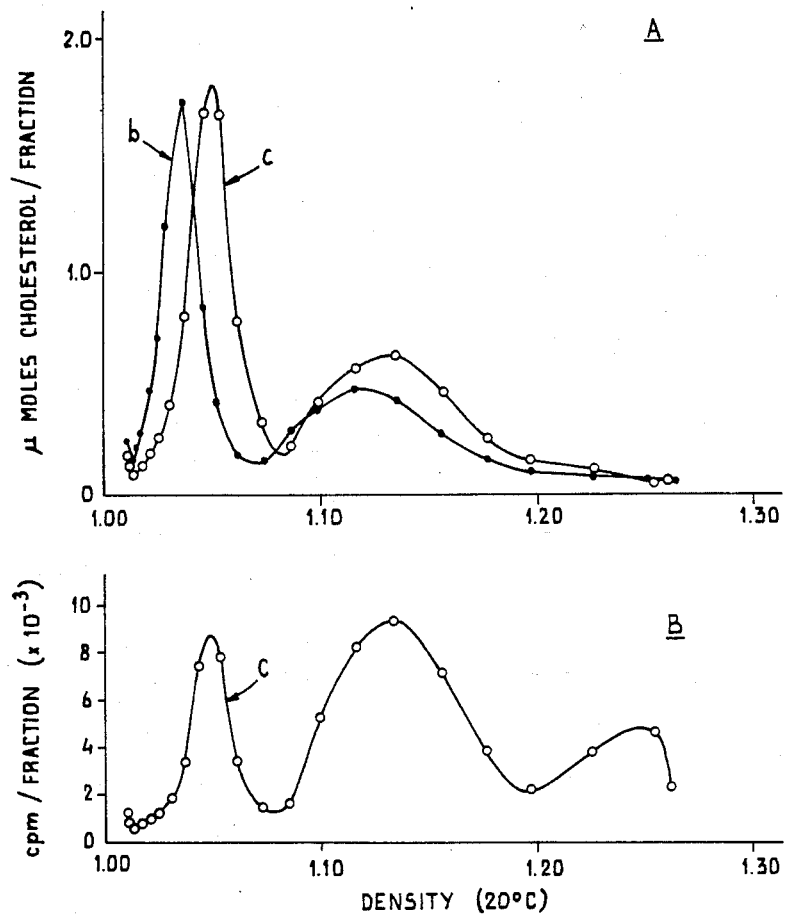

After mixing of a 1 mM solution of the compound having formula 6 in water or in a buffered solution with a suspension of lipide-vesicles or lipoproteins in water or buffered solutions the compound having formula 6 becomes associated with these lipide-containing particles. This appears from the experiments illustrated in FIGS. 1 and 2. In the experiment of FIG. 1 0.2 ml of a 2 mM solution of the compound having formula 6 in water was mixed with 1.8 ml of a suspension of lipide-vesicles containing 3.6 mmol of total lipide (cholesterol and sfingomyeline in the molar ratio of 1:1). In this mixture the compound having formula 6 is present in an amount corresponding to 10% of the present lipide. In the experiment according to FIG. 2 0.2 ml of a 10 mM-solution of the compound having formula 6 in water was mixed with 1.8 ml human blood plasma. To said mixtures 0.75 mg solid KBr was added. After the dissolution of the KBr the mixtures were put in a centrifuge tube after which 3 ml of 9% NaCl, 3 ml of 3% NaCl and 3 ml of 1% NaCl were added carefully. The tubes filled in this way were placed in a rotor of an ultracentrifuge which was operated for 18 hours at 40,000 rpm. After density gradient centrifugation of the compound having formula 6 per se it is found that this compound is present in the fractions having a density of more than 1.20 (curve a in FIG. 1B); lipide-vesicles or lipoproteins per se are present in fractions with a density of less than 1.20 (curve b in FIGS. 1A and 2A). After centrifugation of the mixture of vesicles or lipoproteins and the compound having formula 6 the cholesterol of the vesicles (FIG. 1A, curve c) or of the lipoproteins (FIG. 2A, curve c) as well as the compound having formula 6 (curve c in FIGS. 1B and 2B) are present in fractions having a density of less than 1.20 and in such a way that the distribution of the compound having formula 6 over the fractions shows the same pattern as the distribution of cholesterol. Further it appears that the lipide vesicles or lipoproteins by encapsulating the compound having formula 6 have got a higher density (compare curve c with curve b in FIGS. 1A and 2A).

A water-soluble labelled compound can be encapsulated in the vesicles e.g. $^{14}$C-sucrose. When these vesicles are mixed with the compound having formula 6 in a ratio as described in the above the radio-activity of $^{14}$C-sucrose is almost completely found back in the same fractions and in the same pattern as the cholesterol of the lipide vesicles. This means that the vesicles by association with the compound having formula 6 do not show leakage.

EXAMPLE 4

Figure 3:
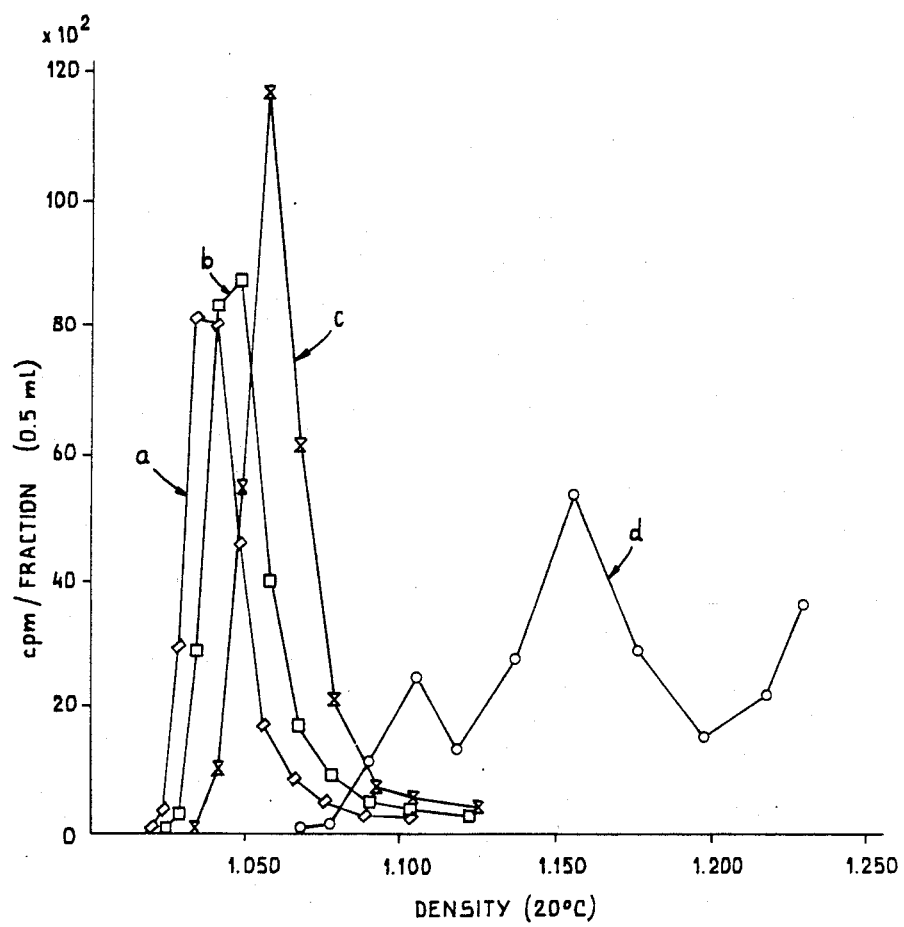

Lipoproteins from human plasma may also be loaded with the compound having formula 6 after they have been isolated from human plasma by density gradient centrifugation. This is illustrated in FIG. 3. The isolated low density lipoprotein (LDL) (the fractions having a density between 1.019 and 1.063) was first labelled with $^{125}$I according to a known procedure, and then mixed in the following ratio's with the compound having formula 6 (dissolved in water): 0 (a), 0.25 (b), 0.65 (c) and 10 (d) $\mu$g of the compound having formula 6 per $\mu$g LDL-protein. From the course of the curves (a) up to (d) it appears that at a ratio of 0.65 the LDL (the protein as well as the cholesterol) is present as the single peak in the density gradient whereas at a ratio of 10 the LDL is disintegrated into a number of new particles having a much higher density.

EXAMPLE 5

Figure 4:
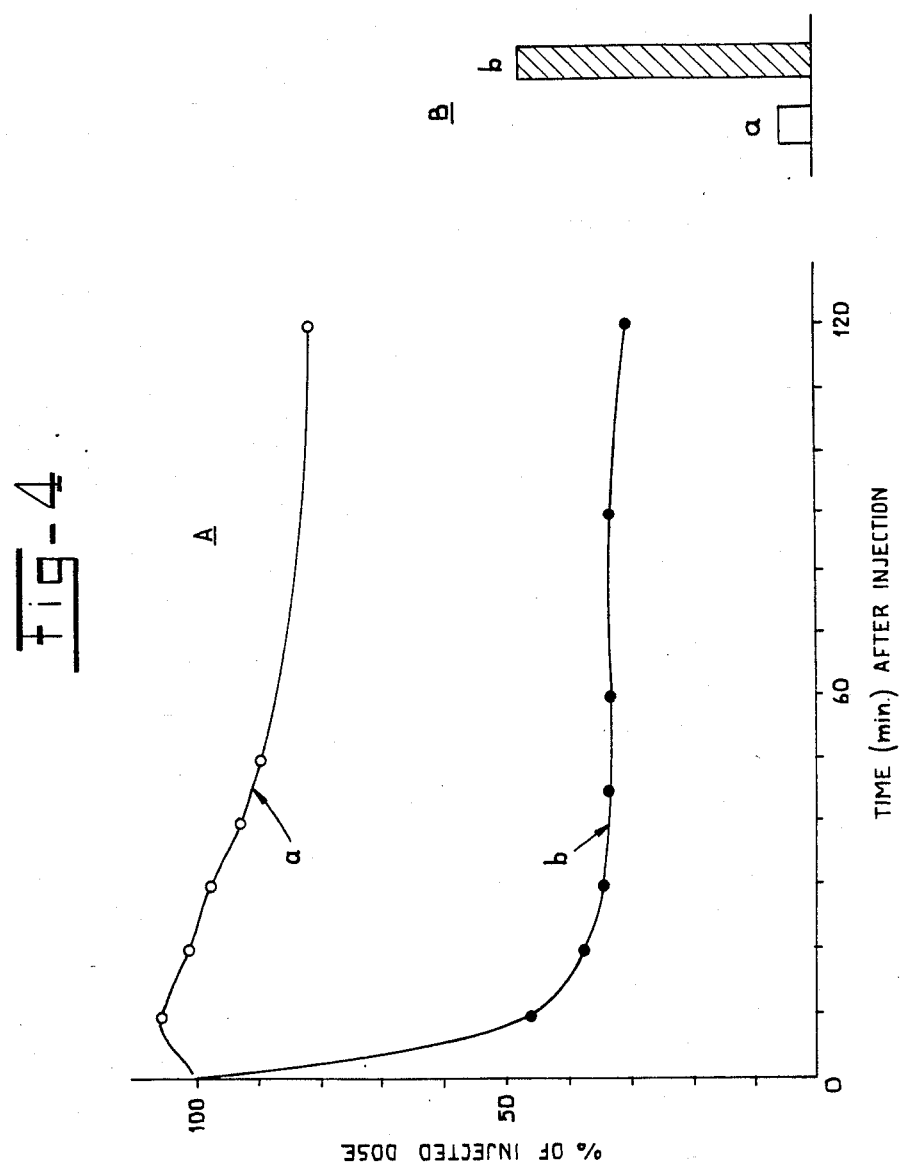

The loading of lipide vesicles of isolated low density lipoprotein with the compound having formula 6 as described in examples 3 and 4 leads to an altered behaviour of these particles after intravenous injection in mammals. This is illustrated in FIGS. 4 and 5. Whereas the unloaded vesicles (labelled by encapsulated $^{14}$C-sucrose) or lipoprotein particles (labelled with $^{125}$I) after intravenous injection in a rat only disappears slowly from the blood (FIGS. 4A and 5A, curve a) and are taken up by the liver in a very small ratio (FIG. 4B, pile a, and FIG. 5B, curve a), the vesicles loaded with the compound having formula 6 were removed in the first half hour after injection about 10 times quicker from the blood (FIG. 4A, curve b) and taken up in the liver (FIG. 4B, pile b). Also LDL disappears after mixing with the compound having formula 6 in a ratio of 0.25 μg of the compound having formula 6/μg LDL-protein or higher with a much greater speed from the blood (FIG. 5A, curves b, c and d) and is taken up by the liver (FIG. 5B, curves b, c and d). Such a result can also be obtained with a compound having formula 7 as well as with the 2-acetamino-2-deoxygalactose derivative.

EXAMPLE 6

The compound having formula 6 is able to reduce the serum-cholesterol level in rats after intravenous administration. For obtaining such a reduction the compound having formula 6 was dissolved in a phosphate buffer salt solution in concentrations of 4 and 8 mg/ml and administered via an infusion pump (pump velocity: 0.6 ml/h) via a catheter in the venous blood stream. When 21.6 mg of the compound having formula 6 was administered in this way in a period of 4 hours the serum-cholesterol level decreased to about half of the starting value and remained at this low value during at least 24 hours (vide FIG. 6, curve a). Administration of smaller amounts of the compound having formula 6 had a corresponding lower effect (curve b). Such a result may also be obtained with the compound having formula 7 as well as the 2-acetamino-2-deoxygalactose derivative.

I claim:

1. Synthetic glycolipides having the general formula lipidyl-O-R, in which the lipidyl moiety is selected from the group consisting of 5-cholesten-3-β-yl, ceramidyl, phosphatidylethanolamine and diacylglyceryl and R represents a group having the formula

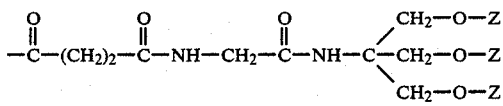

wherein two symbols Z represent a glycopyranosyl rest and the other symbol Z is a hydrogen atom or all three symbols Z represent a glycopyranosyl rest.

2. Glycolipide according to claim 1, characterized in that the glycolipide is N-tris-(β-D-galactopyranosyloxymethyl)methyl-N$^\alpha$(4-(5-cholesten-3β-yloxy)succinyl)-glycinamide.

3. Glycolipide according to claim 1, characterized in that the glycolipide is N-tris-(β-D-2-acetamido-2-deoxygalactopyranosyloxymethyl)methyl-N$^\alpha$(4-(5-cholesten-3β-yloxy)succinylglycinamide.

4. A process for the preparation of glycolipides according to claim 1, characterized by the following stages:

(a) N-(2-hydroxy-(1,1-dihydroxymethyl)-ethyl)-N$^\alpha$-benzyloxycarbonylglycinamide is prepared by reacting 2-amino-2-hydroxymethyl-1,3-propanediol with benzyloxycarbonylglycine in the presence of N-ethoxycarbonyl-2-ethoxy-1,2-dihydroxyquinoline;

(b) per-O-acetyl-D-glycopyranosylbromide is prepared by reacting a per-O-acetyl-D-glycopyranose with PBr$_3$ in acetic anhydride;

(c) N-(tris(per-O-acetyl-D-glycopyranosyloxymethyl)methyl)-N$^\alpha$-benzyloxycarbonylglycinamide is prepared by reacting N-(2-hydroxy-(1,1-dihydroxymethyl)-ethyl)N$^\alpha$-benzyloxycarbonylglycin amide, kept in suspension in CH$_3$CN with Hg(CN)$_2$ and HgBr$_2$ with per-O-acetyl-D-glycopyranosylbromide, dissolved in CH$_3$CN and purifying the product by column chromatography;

(d) N-(tris(per-O-acetyl-D-glycopyranosyloxymethyl)methyl)-N$^\alpha$-benzyloxy carbonylglycinamide is converted into N-(tris-glycopyranosyloxymethyl)methyl)glycine.HCl-salt by treating the compound with subsequently triethanolamine, acetic acid, hydrogen and palladium/carbon and HCl after which the compound is purified by gel filtration;

(e) one of the lipides selected from the group consisting of cholesterol, ceramide, phosphatidylethanolamine and diacylglycerol is reacted with succinic acid in pyridine into the corresponding hemisuccinyl ester and this ester is then converted into the N-hydroxy-succinimidyl-4-(lipidyl)succinate by reacting said ester with N-hydroxy-succinimide in tetrahydrofuran in the presence of dicyclohexylcarbodiimide;

(f) N-(tris(glycopyranosyloxymethyl)methyl-N$^\alpha$-(4-lipidyl)succinylglycinamide is prepared by combining N-(tris(glycopyranosyloxymethyl)methyl)-glycine.HCl dissolved with N-ethylmorpholine in dimethylformamide, with N-hydroxy-succinimidyl-4-(lipidyl)succinate, dissolved in dimethylacetamide; (g) N-tris(glycopyranosyloxymethyl)methyl-N$^\alpha$-(4-lipidyl)succinylglycinamide according to the invention as well as the corresponding bis(-glycopyranosyloxymethyl)-derivative are purified by column chromatography.

5. A process for the preparation of N-tris-(β-D-galactopyranosyloxymethyl)methyl-N$^\alpha$(4-(5-cholesten-3β-yloxy)succinyl)glycinamide characterized by carrying out the process as described in claim 4 using as starting compounds 5-cholesten-3β-ol as lipide in stage e) and penta-O-acetyl-β-D-galactopyranose as acylated monohexose in stage b).

6. Lipide vesicles or lipoproteins having encapsulated therein a glycolipide according to claim 1 characterized by dissolving the glycolipide according to claim 1 in water or aqueous salt solution and mixing this solution with a suspension of lipide vesicles or lipoproteins in water or aqueous salt solution.

7. Lipide vesicles or lipoproteins according to claim 6 characterized in that the glycolipide is N-tris-(β-D-galactopyranosyloxymethyl)methyl-N(4-(5-cholesten-3β-yloxy)succinyl)gylcinamide.

8. A process for solubilizing cholesterol in water or aqueous media characterized by mixing a solution of cholesterol in ethanol with a solution of a glycolipide according to claim 1 in water.

9. A process according to claim 8 characterized in that a solution of cholesterol and ethanol is mixed with a solution of N-tris-($\beta$-D-galactopyranosyloxmethyl)-methyl-N(4-(5-cholesten-3$\beta$-yloxy)succinyl)glycinamide.

10. A process for reducing the cholesterol level in blood plasma of mammals characterized by administering thereto a glycolipide according to claim 1 as solution in an aqueous salt solution by intravenous infusion.

11. A process according to claim 10 characterized in that N-tris-$\beta$-D-galactopyranosyloxmethyl)methyl-N(4-(5-cholesten-3$\beta$-yloxy)succinyl)gylcinamide.

* * * * *